United States Patent
Haishi et al.

(10) Patent No.: US 10,564,235 B2
(45) Date of Patent: Feb. 18, 2020

(54) MRI METHOD AND APPARATUS WITH SYNCHRONIZED CLOCK TIMING FROM THE IMAGING PULSE SEQUENCE

(71) Applicant: MRTechnology, Inc., Tsukuba-shi, Ibaraki (JP)

(72) Inventors: Tomoyuki Haishi, Tsukuba (JP); Seitaro Hashimoto, Tsukuba (JP); Katsumi Kose, Kashiwa (JP)

(73) Assignee: MRTechnology, Inc., Tsukuba-shi (JP)

(*) Notice: Subject to any disclaimer, the term of this patent is extended or adjusted under 35 U.S.C. 154(b) by 1402 days.

(21) Appl. No.: 13/712,108

(22) Filed: Dec. 12, 2012

(65) Prior Publication Data

US 2013/0162248 A1 Jun. 27, 2013

Related U.S. Application Data

(63) Continuation of application No. PCT/JP2011/072079, filed on Sep. 27, 2011.

(51) Int. Cl.
*G01R 33/36* (2006.01)
*G01R 33/54* (2006.01)
(Continued)

(52) U.S. Cl.
CPC .................. *G01R 33/36* (2013.01)

(58) Field of Classification Search
CPC ........ G01R 33/54; G01R 33/28; G01R 33/36; A61B 5/055
(Continued)

(56) References Cited

U.S. PATENT DOCUMENTS 3,530,371 A * 9/1970 Ernst .................. C25D 3/66
324/313
4,284,950 A * 8/1981 Burl .................. G01R 33/24
324/313

(Continued)

FOREIGN PATENT DOCUMENTS

JP S63-132644 6/1988
JP 02-004331 A 1/1990

(Continued)

OTHER PUBLICATIONS

EESR of the corresponding European Patent Application No. 11867573.5 dated Mar. 12, 2015.

(Continued)

Primary Examiner — Melissa J Koval
Assistant Examiner — Tiffany A Fetzner
(74) Attorney, Agent, or Firm — Kratz, Quintos & Hanson, LLP

(57) ABSTRACT

An imaging unit producing images, and a control unit controlling the imaging unit. The imaging device further comprises: a reference clock unit generating a reference clock; and a signal input/output unit provided between the imaging unit and the control unit and inputting and outputting signals in synchronization with the reference clock generated by the reference clock unit. The control unit comprises: generating unit generating a plurality of control signals; transmitting unit transmitting the plural control signals; receiving unit receiving measurement signals; and extraction unit extracting the measurement signal when the reception times of the measurement signals received by the receiving unit agrees with the extraction timing generated by the generating unit.

10 Claims, 11 Drawing Sheets

(51) Int. Cl.
  *G01R 33/28* (2006.01)
  *A61B 5/055* (2006.01)
  *A61B 5/00* (2006.01)

(58) Field of Classification Search
  USPC .......................... 324/300–322; 600/407–435
  See application file for complete search history.

(56) References Cited

U.S. PATENT DOCUMENTS

| | | | |
|---|---|---|---|
| 4,452,250 A | 6/1984 | Chance et al. | |
| 5,004,983 A * | 4/1991 | Proksa | G01R 33/3607 324/322 |
| 5,657,757 A * | 8/1997 | Hurd | G01R 33/4828 324/307 |
| 6,025,717 A * | 2/2000 | Hertz | G01R 33/54 324/307 |
| 6,529,000 B2 * | 3/2003 | Lou | G01R 33/3621 324/309 |
| 6,549,009 B1 * | 4/2003 | Hertz | G01R 33/54 324/307 |
| 6,549,799 B2 * | 4/2003 | Bock | G01R 33/3415 324/307 |
| 7,659,124 B2 * | 2/2010 | Pusiol | G01R 33/441 324/307 |
| 8,174,264 B2 * | 5/2012 | Adachi | G01R 33/3692 324/318 |
| 8,502,540 B2 * | 8/2013 | Nakanishi | G01R 33/3692 324/318 |
| 8,947,091 B2 * | 2/2015 | Nakanishi | G01R 33/3692 324/307 |
| 9,052,367 B2 * | 6/2015 | Akita | G01R 33/3607 |
| 2002/0156362 A1 * | 10/2002 | Bock | G01R 33/3415 600/410 |
| 2005/0202570 A1 * | 9/2005 | Pusiol | G01R 33/441 436/173 |
| 2009/0322335 A1 * | 12/2009 | Adachi | G01R 33/3692 324/318 |
| 2010/0117649 A1 * | 5/2010 | Nakanishi | G01R 33/3692 324/318 |
| 2010/0308826 A1 | 12/2010 | Saes et al. | |
| 2011/0101977 A1 * | 5/2011 | Nakanishi | G01R 33/3692 324/307 |
| 2011/0109316 A1 * | 5/2011 | Akita | G01R 33/3607 324/322 |
| 2013/0162248 A1 * | 6/2013 | Haishi | G01R 33/54 324/307 |

FOREIGN PATENT DOCUMENTS

| | | |
|---|---|---|
| JP | H9-173316 | 7/1997 |
| JP | H10-213557 | 8/1998 |
| JP | 2005-152032 A1 | 6/2005 |
| JP | 2005-288025 A | 10/2005 |

OTHER PUBLICATIONS

International Search Report for International Application PCT/JP2011/072079 dated Sep. 27, 2011.

* cited by examiner

FIG. 3

[PULSE SEQUENCE FILE]

| ROW NUMBER | PULSE SEQUENCE | DESCRIPTION |
|---|---|---|
| 1ST ROW | : NX 1 | NUMBER OF ACCUMULATIONS |
| 2ND ROW | : DW 5 | RECEIVER SAMPLING RATE [μSEC] |
| 3RD ROW | : NR 2048 | NUMBER OF RECEIVER SAMPLING POINTS |
| 4TH ROW | : N0 1 | NUMBER OF PHASE ENCODE 0 |
| 5TH ROW | : N1 128 | NUMBER OF PHASE ENCODE 1 |
| 6TH ROW | : N2 16 | NUMBER OF PHASE ENCODE 2 |
| 7TH ROW | : S0 0 | STEP SIZE OF PHASE ENCODE 0 |
| 8TH ROW | : S1 64 | STEP SIZE OF PHASE ENCODE 1 |
| 9TH ROW | : S2 64 | STEP SIZE OF PHASE ENCODE 2 |
| 10TH ROW | : DU 10 | NUMBER OF DUMMY PULSES |
| 11TH ROW | : TR 100 | REPETITION TIME TR [MSEC] |
| 12TH ROW | 000099400 RF 0002 | TRANSMIT SECOND RF PULSE 9,940 μSEC LATER FROM MEASUREMENT START |
| 13TH ROW | 000101600 GY 8000<-e5 | RENEW AND OUTPUT GRADIENT MAGNETIC FIELD GY AXIS CONTROL SIGNAL 10,160 μSEC FROM MEASUREMENT START |
| 14TH ROW | 000102200 GX 6E40 | OUTPUT 6E40 TO GRADIENT MAGNETIC FIELD GX AXIS CONTROL SIGNAL 10,220 μSEC LATER FROM MEASUREMENT START |
| 15TH ROW | 000102600 GZ 8000<-e6 | RENEW AND OUTPUT GRADIENT MAGNETIC FIELD GZ AXIS 10,260 μSEC LATER FROM MEASUREMENT START |
| 16TH ROW | 000120320 GZ 8000 | OUTPUT 8000 TO GRADIENT MAGNETIC FIELD GZ AXIS CONTROL SIGNAL 12,032 μSEC LATER FROM MEASUREMENT START |
| 17TH ROW | 000128260 GY 8000 | OUTPUT 8000 TO GRADIENT MAGNETIC FIELD GY AXIS CONTROL SIGNAL 12,826 μSEC LATER FROM MEASUREMENT START |
| 18TH ROW | 000133800 GX 88D4 | OUTPUT 88D4 TO GRADIENT MAGNETIC FIELD GX AXIS CONTROL SIGNAL 13,380 μSEC LATER FROM MEASUREMENT START |
| 19TH ROW | 000148800 AD 0000 | START OF RECEIPT BY A/D CONVERSION OF RECEIVED SIGNALS 14,880 μSEC LATER FROM MEASUREMENT START |
| 20TH ROW | 000302400 GX 8000 | OUTPUT 8000 TO GRADIENT MAGNETIC FIELD GX AXIS CONTROL SIGNAL 30,240 μSEC LATER FROM MEASUREMENT START |
| ... | ... | ... |
| ... | ... | ... |
| ... | ... | ... |
| ... | ... | ... |
| ... | ... | ... |
| ... | ... | ... |
| ... | ... | ... |
| ... | ... | ... |
| ... | ... | ... |

FIG. 4

[CONTROL SIGNAL (TRANSMIT DATA)]

| DATA NUMBER | TIME FROM START OF CONTROL SIGNAL | CONTROL SIGNAL (TRANSMIT DATA) |
|---|---|---|
| 0 | 0000000 [μsec] | 4E18,0000,0000,0000,0000,0000,0000,0000 |
| 1 | 0000001 [μsec] | 4E18,0000,0000,0000,0000,0000,0000,0000 |
| 2 | 0000002 [μsec] | 4E18,0000,0000,0000,0000,0000,0000,0000 |
| 3 | 0000003 [μsec] | 4E18,0000,0000,0000,0000,0000,0000,0000 |
| 4 | 0000004 [μsec] | 4E18,0000,0000,0000,0000,0000,0000,0000 |
| 5 | 0000005 [μsec] | 4E18,0000,0000,0000,0000,0000,0000,0000 |
| 6 | 0000006 [μsec] | 4E18,0000,0000,0000,0000,0000,0000,0000 |
| 7 | 0000007 [μsec] | 4E18,0000,0000,0000,0000,0000,0000,0000 |
| 8 | 0000008 [μsec] | 4E18,0000,0000,0000,0000,0000,0000,0000 |
| 9 | 0000009 [μsec] | 4E18,0000,0000,0000,0000,0000,0000,0000 |
| 10 | 00000010 [μsec] | 4E18,0000,0000,0000,0000,0000,0000,0000 |
| 11 | 00000011 [μsec] | 4E18,0000,0000,0000,0000,0000,0000,0000 |
| 12 | 00000012 [μsec] | 4E18,0000,0000,0000,0000,0000,0000,0000 |
| 13 | 00000013 [μsec] | 4E18,0000,0000,0000,0000,0000,0000,0000 |
| 14 | 00000014 [μsec] | 4E18,0000,0000,0000,0000,0000,0000,0000 |
| 15 | 00000015 [μsec] | 4E18,0000,0000,0000,0000,0000,0000,0000 |
| 16 | 00000016 [μsec] | 4E18,0000,0000,0000,0000,0000,0000,0000 |
| 17 | 00000017 [μsec] | 4E18,0000,0000,0000,0000,0000,0000,0000 |
| 18 | 00000018 [μsec] | 4E18,0000,0000,0000,0000,0000,0000,0000 |
| 19 | 00000019 [μsec] | 4E18,0000,0000,0000,0000,0000,0000,0000 |
| 20 | 00000020 [μsec] | 4E18,0000,0000,0000,0000,0000,0000,0000 |
| 21 | 00000021 [μsec] | 4E18,0000,0000,0000,0000,0000,0000,0000 |
| 22 | 00000022 [μsec] | 4E18,0000,0000,0000,0000,0000,0000,0000 |
| 23 | 00000023 [μsec] | 4E18,0000,0000,0000,0000,0000,0000,0000 |
| 24 | 00000024 [μsec] | 4E18,0000,0000,0000,0000,0000,0000,0000 |
| 25 | 00000025 [μsec] | 4E18,0000,0000,0000,0000,0000,0000,0000 |
| 26 | 00000026 [μsec] | 4E18,0000,0000,0000,0000,0000,0000,0000 |
| 27 | 00000027 [μsec] | 4E18,0000,0000,0000,0000,0000,0000,0000 |
| 28 | 00000028 [μsec] | 4E18,0000,0000,0000,0000,0000,0000,0000 |
| 29 | 00000029 [μsec] | 4E18,0000,0000,0000,0000,0000,0000,0000 |
| 30 | 00000030 [μsec] | 4E18,0000,0000,0000,0000,0000,0000,0000 |
| 31 | 00000031 [μsec] | 4E18,0000,0000,0000,0000,0000,0000,0000 |
| 32 | 00000032 [μsec] | 4E18,0000,0000,0000,0000,0000,0000,0000 |
| 33 | 00000033 [μsec] | 4E18,0000,0000,0000,0000,0000,0000,0000 |
| 34 | 00000034 [μsec] | 4E18,0000,0000,0000,0000,0000,0000,0000 |
| 35 | 00000035 [μsec] | 4E18,0000,0000,0000,0000,0000,0000,0000 |
| 36 | 00000036 [μsec] | 4E18,0000,0000,0000,0000,0000,0000,0000 |
| 37 | 00000037 [μsec] | 4E18,0000,0000,0000,0000,0000,0000,0000 |
| 38 | 00000038 [μsec] | 4E18,0000,0000,0000,0000,0000,0000,0000 |
| 39 | 00000039 [μsec] | 4E18,0000,0000,0000,0000,0000,0000,0000 |
| 40 | 00000040 [μsec] | 4E18,0000,0000,0000,0000,0000,0000,0000 |
| 41 | 00000041 [μsec] | 4E18,0000,0000,0000,0000,0000,0000,0000 |
| 42 | 00000042 [μsec] | 4E18,0000,0000,0000,0000,0000,0000,0000 |
| 43 | 00000043 [μsec] | 4E18,0000,0000,0000,0000,0000,0000,0000 |
| 44 | 00000044 [μsec] | 4E18,0000,0000,0000,0000,0000,0000,0000 |
| 45 | 00000045 [μsec] | 4E18,0000,0000,0000,0000,0000,0000,0000 |
| 46 | 00000046 [μsec] | 4E18,0000,0000,0000,0000,0000,0000,0000 |
| 47 | 00000047 [μsec] | 4E18,0000,0000,0000,0000,0000,0000,0000 |
| 48 | 00000048 [μsec] | 4E18,0000,0000,0000,0000,0000,0000,0000 |
| 49 | 00000049 [μsec] | 4E18,0000,0000,0000,0000,0000,0000,0000 |
| 50 | 00000050 [μsec] | 4E18,0000,0000,0000,0000,0000,0000,0000 |
| 51 | 00000051 [μsec] | 4E18,0000,0000,0000,0000,0000,0000,0000 |
| ... | ... | ... |
| ... | ... | ... |
| ... | ... | ... |
| ... | ... | ... |

FIG. 5

[CONTROL SIGNAL (TRANSMIT DATA)]

| DATA NUMBER | TIME FROM START OF CONTROL SIGNAL | CONTROL SIGNAL (TRANSMIT DATA) |
|---|---|---|
| 0 | 0000000 [μsec] | 4E18,0000,0000,0000,0000,0000,0000,0000 |
| 1 | 0000001 [μsec] | 4E18,0000,0000,0000,0000,0000,0000,0000 |
| 2 | 0000002 [μsec] | 4E18,0000,0000,0000,0000,0000,0000,0000 |
| 3 | 0000003 [μsec] | 4E18,0000,0000,0000,0000,0000,0000,0000 |
| 4 | 0000004 [μsec] | 4E18,0000,0000,0000,0000,0000,0000,0000 |
| 5 | 0000005 [μsec] | 4E18,0000,0000,0000,0000,0000,0000,0000 |
| 6 | 0000006 [μsec] | 4E18,0000,0000,0000,0000,0000,0000,0000 |
| 7 | 0000007 [μsec] | 4E18,0000,0000,0000,0000,0000,0000,0000 |
| 8 | 0000008 [μsec] | 4E18,0000,0000,0000,0000,0000,0000,0000 |
| 9 | 0000009 [μsec] | 4E18,0000,0000,0000,0000,0000,0000,0000 |
| ... | ... | ... |
| ... | ... | ... |
| ... | ... | ... |
| ... | ... | ... |
| 14860 | 00014860 [μsec] | 4E18,0000,0000,0000,08D4,0000,0000,0000 |
| 14861 | 00014861 [μsec] | 4E18,0000,0000,0000,08D4,0000,0000,0000 |
| 14862 | 00014862 [μsec] | 4E18,0000,0000,0000,08D4,0000,0000,0000 |
| 14863 | 00014863 [μsec] | 4E18,0000,0000,0000,08D4,0000,0000,0000 |
| 14864 | 00014864 [μsec] | 4E18,0000,0000,0000,08D4,0000,0000,0000 |
| 14865 | 00014865 [μsec] | 4E18,0000,0000,0000,08D4,0000,0000,0000 |
| 14866 | 00014866 [μsec] | 4E18,0000,0000,0000,08D4,0000,0000,0000 |
| 14867 | 00014867 [μsec] | 4E18,0000,0000,0000,08D4,0000,0000,0000 |
| 14868 | 00014868 [μsec] | 4E18,0000,0000,0000,08D4,0000,0000,0000 |
| 14869 | 00014869 [μsec] | 4E18,0000,0000,0000,08D4,0000,0000,0000 |
| 14870 | 00014870 [μsec] | 4E18,0000,0000,0000,08D4,0000,0000,0000 |
| 14871 | 00014871 [μsec] | 4E18,0000,0000,0000,08D4,0000,0000,0000 |
| 14872 | 00014872 [μsec] | 4E18,0000,0000,0000,08D4,0000,0000,0000 |
| 14873 | 00014873 [μsec] | 4E18,0000,0000,0000,08D4,0000,0000,0000 |
| 14874 | 00014874 [μsec] | 4E18,0000,0000,0000,08D4,0000,0000,0000 |
| 14875 | 00014875 [μsec] | 4E18,0000,0000,0000,08D4,0000,0000,0000 |
| 14876 | 00014876 [μsec] | 4E18,0000,0000,0000,08D4,0000,0000,0000 |
| 14877 | 00014877 [μsec] | 4E18,0000,0000,0000,08D4,0000,0000,0000 |
| 14878 | 00014878 [μsec] | 4E18,0000,0000,0000,08D4,0000,0000,0000 |
| 14879 | 00014879 [μsec] | 4E18,0000,0000,0000,08D4,0000,0000,0000 |
| 14880 | 00014880 [μsec] | 4E18,0000,0000,0000,08D4,0000,0000,0000 |
| 14881 | 00014881 [μsec] | 4E18,0000,0000,0000,08D4,0000,0000,0000 |
| 14882 | 00014882 [μsec] | 4E18,0000,0000,0000,08D4,0000,0000,0000 |
| 14883 | 00014883 [μsec] | 4E18,0000,0000,0000,08D4,0000,0000,0000 |
| 14884 | 00014884 [μsec] | 4E18,0000,0000,0000,08D4,0000,0000,0000 |
| 14885 | 00014885 [μsec] | 4E18,0000,0000,0000,08D4,0000,0000,0000 |
| 14886 | 00014886 [μsec] | 4E18,0000,0000,0000,08D4,0000,0000,0000 |
| 14887 | 00014887 [μsec] | 4E18,0000,0000,0000,08D4,0000,0000,0000 |
| 14888 | 00014888 [μsec] | 4E18,0000,0000,0000,08D4,0000,0000,0000 |
| 14889 | 00014889 [μsec] | 4E18,0000,0000,0000,08D4,0000,0000,0000 |
| 14890 | 00014890 [μsec] | 4E18,0000,0000,0000,08D4,0000,0000,0000 |
| 14891 | 00014891 [μsec] | 4E18,0000,0000,0000,08D4,0000,0000,0000 |
| 14892 | 00014892 [μsec] | 4E18,0000,0000,0000,08D4,0000,0000,0000 |
| 14893 | 00014893 [μsec] | 4E18,0000,0000,0000,08D4,0000,0000,0000 |
| 14894 | 00014894 [μsec] | 4E18,0000,0000,0000,08D4,0000,0000,0000 |
| 14895 | 00014895 [μsec] | 4E18,0000,0000,0000,08D4,0000,0000,0000 |
| 14896 | 00014896 [μsec] | 4E18,0000,0000,0000,08D4,0000,0000,0000 |
| 14897 | 00014897 [μsec] | 4E18,0000,0000,0000,08D4,0000,0000,0000 |
| 14898 | 00014898 [μsec] | 4E18,0000,0000,0000,08D4,0000,0000,0000 |
| 14899 | 00014899 [μsec] | 4E18,0000,0000,0000,08D4,0000,0000,0000 |
| 14900 | 00014900 [μsec] | 4E18,0000,0000,0000,08D4,0000,0000,0000 |
| ... | ... | ... |
| ... | ... | ... |
| ... | ... | ... |
| ... | ... | ... |

FIG. 6

[EXTRACTION START TIMETABLE]

| ROW NUMBER | EXTRACTION START TIME [μSEC] |
|---|---|
| 1ST ROW | 14880 |
| 2ND ROW | 114880 |
| 3RD ROW | 214880 |
| 4TH ROW | 314880 |
| 5TH ROW | 414880 |
| 6TH ROW | 514880 |
| 7TH ROW | 614880 |
| 8TH ROW | 714880 |
| 9TH ROW | 814880 |
| 10TH ROW | 914880 |
| 11TH ROW | 1014880 |
| 12TH ROW | 1114880 |
| 13TH ROW | 1214880 |
| 14TH ROW | 1314880 |
| 15TH ROW | 1414880 |
| 16TH ROW | 1514880 |
| 17TH ROW | 1614880 |
| 18TH ROW | 1714880 |
| 19TH ROW | 1814880 |
| 20TH ROW | 1914880 |
| 21TH ROW | 2014880 |
| 22TH ROW | 2114880 |
| 23TH ROW | 2214880 |
| 24TH ROW | 2314880 |
| 25TH ROW | 2414880 |
| ... | ... |
| ... | ... |
| ... | ... |
| ... | ... |
| ... | ... |

FIG. 7

[MEASUREMENT SIGNAL (RECEIVED DATA)]

| DATA NUMBER | TIME FROM START OF MEASUREMENT SIGNAL RECEPTION | MEASUREMENT SIGNAL (RECEIVED DATA) |
|---|---|---|
| 0 | 0000000 [μsec] | B1E7,0000,-54,-26,0,1,0000,0000 |
| 1 | 0000001 [μsec] | B1E7,0000,-54,-21,0,2,0000,0000 |
| 2 | 0000002 [μsec] | B1E7,0000,-54,-16,0,3,0000,0000 |
| 3 | 0000003 [μsec] | B1E7,0000,-52,-11,0,4,0000,0000 |
| 4 | 0000004 [μsec] | B1E7,0000,-50,-7,0,5,0000,0000 |
| 5 | 0000005 [μsec] | B1E7,0000,-49,-6,0,6,0000,0000 |
| 6 | 0000006 [μsec] | B1E7,0000,-43,-4,0,7,0000,0000 |
| 7 | 0000007 [μsec] | B1E7,0000,-38,-6,0,8,0000,0000 |
| 8 | 0000008 [μsec] | B1E7,0000,-31,-7,0,9,0000,0000 |
| 9 | 0000009 [μsec] | B1E7,0000,-23,-11,0,10,0000,0000 |
| 10 | 00000010 [μsec] | B1E7,0000,-13,-14,0,11,0000,0000 |
| 11 | 00000011 [μsec] | B1E7,0000,-2,-21,0,12,0000,0000 |
| 12 | 00000012 [μsec] | B1E7,0000,10,-26,0,13,0000,0000 |
| 13 | 00000013 [μsec] | B1E7,0000,24,-33,0,14,0000,0000 |
| 14 | 00000014 [μsec] | B1E7,0000,37,-40,0,15,0000,0000 |
| 15 | 00000015 [μsec] | B1E7,0000,53,-47,0,16,0000,0000 |
| 16 | 00000016 [μsec] | B1E7,0000,65,-52,0,17,0000,0000 |
| 17 | 00000017 [μsec] | B1E7,0000,79,-57,0,18,0000,0000 |
| 18 | 00000018 [μsec] | B1E7,0000,91,-61,0,19,0000,0000 |
| 19 | 00000019 [μsec] | B1E7,0000,99,-64,0,20,0000,0000 |
| 20 | 00000020 [μsec] | B1E7,0000,108,-64,0,21,0000,0000 |
| 21 | 00000021 [μsec] | B1E7,0000,113,-62,0,22,0000,0000 |
| 22 | 00000022 [μsec] | B1E7,0000,116,-61,0,23,0000,0000 |
| 23 | 00000023 [μsec] | B1E7,0000,116,-57,0,24,0000,0000 |
| 24 | 00000024 [μsec] | B1E7,0000,113,-52,0,25,0000,0000 |
| 25 | 00000025 [μsec] | B1E7,0000,110,-47,0,26,0000,0000 |
| 26 | 00000026 [μsec] | B1E7,0000,103,-40,0,27,0000,0000 |
| 27 | 00000027 [μsec] | B1E7,0000,94,-33,0,28,0000,0000 |
| 28 | 00000028 [μsec] | B1E7,0000,84,-25,0,29,0000,0000 |
| 29 | 00000029 [μsec] | B1E7,0000,72,-18,0,30,0000,0000 |
| 30 | 00000030 [μsec] | B1E7,0000,60,-11,0,31,0000,0000 |
| 31 | 00000031 [μsec] | B1E7,0000,48,-6,0,32,0000,0000 |
| 32 | 00000032 [μsec] | B1E7,0000,36,0,0,33,0000,0000 |
| 33 | 00000033 [μsec] | B1E7,0000,25,1,0,34,0000,0000 |
| 34 | 00000034 [μsec] | B1E7,0000,15,3,0,35,0000,0000 |
| 35 | 00000035 [μsec] | B1E7,0000,6,3,0,36,0000,0000 |
| 36 | 00000036 [μsec] | B1E7,0000,0,1,0,37,0000,0000 |
| 37 | 00000037 [μsec] | B1E7,0000,-4,-4,0,38,0000,0000 |
| 38 | 00000038 [μsec] | B1E7,0000,-7,-7,0,39,0000,0000 |
| 39 | 00000039 [μsec] | B1E7,0000,-11,-14,0,40,0000,0000 |
| 40 | 00000040 [μsec] | B1E7,0000,-11,-21,0,41,0000,0000 |
| 41 | 00000041 [μsec] | B1E7,0000,-11,-26,0,42,0000,0000 |
| 42 | 00000042 [μsec] | B1E7,0000,-11,-33,0,43,0000,0000 |
| 43 | 00000043 [μsec] | B1E7,0000,-11,-40,0,44,0000,0000 |
| 44 | 00000044 [μsec] | B1E7,0000,-11,-47,0,45,0000,0000 |
| 45 | 00000045 [μsec] | B1E7,0000,-11,-50,0,46,0000,0000 |
| 46 | 00000046 [μsec] | B1E7,0000,-11,-54,0,47,0000,0000 |
| 47 | 00000047 [μsec] | B1E7,0000,-11,-55,0,48,0000,0000 |
| 48 | 00000048 [μsec] | B1E7,0000,-13,-57,0,49,0000,0000 |
| 49 | 00000049 [μsec] | B1E7,0000,-14,-55,0,50,0000,0000 |
| 50 | 00000050 [μsec] | B1E7,0000,-18,-52,0,51,0000,0000 |
| 51 | 00000051 [μsec] | B1E7,0000,-21,-47,0,52,0000,0000 |
| ... | ... | ... |
| ... | ... | ... |
| ... | ... | ... |
| ... | ... | ... |

FIG. 8

[RECEIVED DATA]

| DATA NUMBER | TIME FROM START OF MEASUREMENT SIGNAL RECEPTION | MEASUREMENT SIGNAL (RECEIVED DATA) |
|---|---|---|
| 0 | 0000000 [μsec] | B1E7,0000,-54,-26,0,1,0000,0000 |
| 1 | 0000001 [μsec] | B1E7,0000,-54,-21,0,2,0000,0000 |
| 2 | 0000002 [μsec] | B1E7,0000,-54,-16,0,3,0000,0000 |
| 3 | 0000003 [μsec] | B1E7,0000,-52,-11,0,4,0000,0000 |
| 4 | 0000004 [μsec] | B1E7,0000,-50,-7,0,5,0000,0000 |
| 5 | 0000005 [μsec] | B1E7,0000,-49,-6,0,6,0000,0000 |
| 6 | 0000006 [μsec] | B1E7,0000,-43,-4,0,7,0000,0000 |
| 7 | 0000007 [μsec] | B1E7,0000,-38,-6,0,8,0000,0000 |
| 8 | 0000008 [μsec] | B1E7,0000,-31,-7,0,9,0000,0000 |
| 9 | 0000009 [μsec] | B1E7,0000,-23,-11,0,10,0000,0000 |
| ... | ... | ... |
| ... | ... | ... |
| ... | ... | ... |
| ... | ... | ... |
| 14860 | 00014860 [μsec] | B1E7,0000,-6,-30,0,14861,0000,0000 |
| 14861 | 00014861 [μsec] | B1E7,0000,-7,-40,0,14862,0000,0000 |
| 14862 | 00014862 [μsec] | B1E7,0000,-7,-52,0,14863,0000,0000 |
| 14863 | 00014863 [μsec] | B1E7,0000,-9,-62,0,14864,0000,0000 |
| 14864 | 00014864 [μsec] | B1E7,0000,-7,-73,0,14865,0000,0000 |
| 14865 | 00014865 [μsec] | B1E7,0000,-7,-81,0,14866,0000,0000 |
| 14866 | 00014866 [μsec] | B1E7,0000,-6,-88,0,14867,0000,0000 |
| 14867 | 00014867 [μsec] | B1E7,0000,-4,-93,0,14868,0000,0000 |
| 14868 | 00014868 [μsec] | B1E7,0000,-2,-97,0,14869,0000,0000 |
| 14869 | 00014869 [μsec] | B1E7,0000,0,-98,0,14870,0000,0000 |
| 14870 | 00014870 [μsec] | B1E7,0000,3,-97,0,14871,0000,0000 |
| 14871 | 00014871 [μsec] | B1E7,0000,6,-95,0,14872,0000,0000 |
| 14872 | 00014872 [μsec] | B1E7,0000,10,-90,0,14873,0000,0000 |
| 14873 | 00014873 [μsec] | B1E7,0000,13,-85,0,14874,0000,0000 |
| 14874 | 00014874 [μsec] | B1E7,0000,17,-78,0,14875,0000,0000 |
| 14875 | 00014875 [μsec] | B1E7,0000,20,-71,0,14876,0000,0000 |
| 14876 | 00014876 [μsec] | B1E7,0000,24,-64,0,14877,0000,0000 |
| 14877 | 00014877 [μsec] | B1E7,0000,27,-57,0,14878,0000,0000 |
| 14878 | 00014878 [μsec] | B1E7,0000,29,-52,0,14879,0000,0000 |
| 14879 | 00014879 [μsec] | B1E7,0000,32,-47,0,14880,0000,0000 |
| 14880 | 00014880 [μsec] | B1E7,0000,34,-42,0,14881,0000,0000 |
| 14881 | 00014881 [μsec] | B1E7,0000,34,-40,0,14882,0000,0000 |
| 14882 | 00014882 [μsec] | B1E7,0000,32,-38,0,14883,0000,0000 |
| 14883 | 00014883 [μsec] | B1E7,0000,30,-38,0,14884,0000,0000 |
| 14884 | 00014884 [μsec] | B1E7,0000,29,-40,0,14885,0000,0000 |
| 14885 | 00014885 [μsec] | B1E7,0000,25,-42,0,14886,0000,0000 |
| 14886 | 00014886 [μsec] | B1E7,0000,20,-45,0,14887,0000,0000 |
| 14887 | 00014887 [μsec] | B1E7,0000,17,-50,0,14888,0000,0000 |
| 14888 | 00014888 [μsec] | B1E7,0000,12,-55,0,14889,0000,0000 |
| 14889 | 00014889 [μsec] | B1E7,0000,6,-59,0,14890,0000,0000 |
| 14890 | 00014890 [μsec] | B1E7,0000,1,-64,0,14891,0000,0000 |
| 14891 | 00014891 [μsec] | B1E7,0000,-2,-69,0,14892,0000,0000 |
| 14892 | 00014892 [μsec] | B1E7,0000,-6,-73,0,14893,0000,0000 |
| 14893 | 00014893 [μsec] | B1E7,0000,-7,-74,0,14894,0000,0000 |
| 14894 | 00014894 [μsec] | B1E7,0000,-7,-74,0,14895,0000,0000 |
| 14895 | 00014895 [μsec] | B1E7,0000,-7,-74,0,14896,0000,0000 |
| 14896 | 00014896 [μsec] | B1E7,0000,-6,-73,0,14897,0000,0000 |
| 14897 | 00014897 [μsec] | B1E7,0000,-2,-69,0,14898,0000,0000 |
| 14898 | 00014898 [μsec] | B1E7,0000,3,-64,0,14899,0000,0000 |
| 14899 | 00014899 [μsec] | B1E7,0000,8,-59,0,14900,0000,0000 |
| 14900 | 00014900 [μsec] | B1E7,0000,15,-52,0,14901,0000,0000 |
| ... | ... | ... |
| ... | ... | ... |
| ... | ... | ... |
| ... | ... | ... |

FIG. 9

[MEASUREMENT DATA]

| TIME FORM MEASUREMENT START | MEASUREMENT SIGNAL (RECEIVED DATA) |
|---|---|
| ... | ... |
| ... | ... |
| ... | ... |
| ... | ... |
| 00014880 [μsec] | B1E7,0000,34,-42,0,14881,0000,0000 |
| 00014885 [μsec] | B1E7,0000,25,-42,0,14886,0000,0000 |
| 00014890 [μsec] | B1E7,0000,1,-64,0,14891,0000,0000 |
| 00014895 [μsec] | B1E7,0000,-7,-74,0,14896,0000,0000 |
| 00014900 [μsec] | B1E7,0000,15,-52,0,14901,0000,0000 |
| 00014905 [μsec] | B1E7,0000,58,-14,0,14906,0000,0000 |
| 00014910 [μsec] | B1E7,0000,94,15,0,14911,0000,0000 |
| 00014915 [μsec] | B1E7,0000,106,29,0,14916,0000,0000 |
| 00014920 [μsec] | B1E7,0000,94,37,0,14921,0000,0000 |
| 00014925 [μsec] | B1E7,0000,60,37,0,14926,0000,0000 |
| ... | ... |
| ... | ... |
| ... | ... |
| ... | ... |
| ... | ... |
| ... | ... |
| ... | ... |
| 00114880 [μsec] | B1E7,0000,5,-11,1,49345,0000,0000 |
| 00114885 [μsec] | B1E7,0000,-28,-35,1,49350,0000,0000 |
| 00114890 [μsec] | B1E7,0000,-59,-62,1,49355,0000,0000 |
| 00114895 [μsec] | B1E7,0000,-68,-66,1,49360,0000,0000 |
| 00114900 [μsec] | B1E7,0000,-55,-28,1,49365,0000,0000 |
| 00114905 [μsec] | B1E7,0000,-50,32,1,49370,0000,0000 |
| 00114910 [μsec] | B1E7,0000,-64,72,1,49375,0000,0000 |
| 00114915 [μsec] | B1E7,0000,-80,75,1,49380,0000,0000 |
| 00114920 [μsec] | B1E7,0000,-83,67,1,49385,0000,0000 |
| 00114925 [μsec] | B1E7,0000,-78,51,1,49390,0000,0000 |
| ... | ... |
| ... | ... |
| ... | ... |
| ... | ... |
| ... | ... |
| ... | ... |
| ... | ... |

MRI METHOD AND APPARATUS WITH SYNCHRONIZED CLOCK TIMING FROM THE IMAGING PULSE SEQUENCE

CROSS-REFERENCE TO RELATED APPLICATION

This application is a continuation application of International Application No. PCT/JP2011/072079 filed on Sep. 27, 2011. The content of the prior application is herein incorporated by reference in its entirety.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable.

STATEMENT REGARDING PRIOR DISCLOSURES BY THE INVENTOR OR A JOINT INVENTOR

Not Applicable.

BACKGROUND OF THE INVENTION

Technical Field

The present invention relates to an imaging device and an imaging method, more specifically, an imaging device and an imaging method using the nuclear magnetic resonance imaging, which images in vivo information by using the nuclear magnetic resonance phenomenon.

Background Art

Recently, the MRI (Magnetic Resonance Imaging) device using the MRI, which images in vivo information by using the NMR (Nuclear Magnetic Resonance) phenomenon, is noted.

In the conventional MRI device, the pulse generator corresponding to a clock of the MRI measurement must generate stable and accurate pulses at high speed and, for this, special-purpose hardware such as a DSP (Digital Signal Processor), an FPGA (Field-Programmable Gate Array) or others, has been used (refer to Patent Reference 1 and 2).

PATENT REFERENCES

Patent Reference 1: Japanese Patent Application Unexamined Publication No. 09-173316

Patent Reference 2: Japanese Patent Application Unexamined Publication No. 10-213557

BRIEF SUMMARY OF THE INVENTION

Problems to be Solved by the Invention

Such conventional MRI device has a problem that the pulse generator, which is special hardware, is not readily replaceable, and the capacity of the MRI device cannot meet requirements of the pulse sequences which advance day by day.

It has been tried to provide the pulse generator by a general-purpose personal computer, but the OS mounted on the general-purpose personal computer, specifically, the multi-task OS such as Windows (registered trademark) by Microsoft Corporation irregularly executes interruptions, which has made it difficult for the MRI device to generate stable and accurate RF pulses and gradient magnetic field pulses.

An object of the present invention is to provide an imaging device and an imaging method which can produce images by generating pulses of stable and accurate time resolution without using special-purpose hardware.

Means for Solving the Problem

The imaging device according to one aspect of the present invention is the imaging device including an imaging unit producing images, and a control unit controlling the imaging unit, further comprising: a reference clock unit generating a reference clock; and a signal input/output unit provided between the imaging unit and the control unit and inputting and outputting signals in synchronization with the reference clock generated by the reference clock unit, the control unit comprising: generating means generating a plurality of control signals for controlling the imaging unit and generating an extraction timing of extracting measurement signals from the imaging unit; transmitting means transmitting the plural control signals generated by the generating means to the imaging unit via the signal input/output unit in synchronization with the reference clock; receiving means receiving measurement signals from the imaging unit via the signal input/output unit in synchronization with the reference clock and counting reception times of the measurement signals; and extraction means extracting the measurement signal when the reception times of the measurement signals received by the receiving means agrees with the extraction timing generated by the generating means.

In the imaging device described above, it is possible that the generating means generates the plural control signals for controlling the imaging unit, based on a 1st pulse sequence for controlling the imaging unit, and extracts the measurement signal from the imaging unit, based on a 2nd pulse sequence for extracting the measurement signals from the imaging unit.

In the imaging device described above, it is possible that the reference clock includes a first reference clock, and a second reference clock which is different from the first reference clock in the frequency, the transmitting means transmits the plural control means to the imaging unit in synchronization with the first reference clock, and the receiving means receives the measurement signals in synchronization with the second reference clock.

In the imaging device described above, it is possible that the imaging unit is an MRI unit producing images by the nuclear magnetic resonance imaging, and the frequency of the reference clock is in the range of 0.1-2.0 MHz.

In the imaging device described above, it is possible that the imaging device further comprises an external synchronization clock unit generating an external synchronization clock, the control unit further comprising an external synchronization means controlling signal input/output by the signal input/output unit in synchronization with the external synchronization clock generated by the external synchronization clock unit.

The measuring device described according to one aspect of the present invention is the measuring device including a measuring unit for measurement, and a control unit controlling the measuring unit, further comprising: a reference clock unit generating a reference clock; and a signal input/output unit provided between the measuring unit and the control unit and inputting and outputting signals in synchronization with the reference clock generated by the reference clock unit, the control unit comprising: generating means generating a plurality of control signals for controlling the measuring unit and generating an extraction timing of extracting measurement signals from the measuring unit; transmitting means transmitting the plural control signals generated by the generating means via the signal input/output unit in synchronization with the reference clock; receiving means measurement signals from the measuring unit via the signal input/output unit in synchronization with the reference clock and counting a reception numbers of the measurement signals; and extraction means extracting the measurement signal when the reception number of the measurement signals received by the receiving means agrees with the extraction timing generated by the generating means.

The imaging method according to one aspect to the present invention is the imaging method of producing images by an imaging unit comprising: generating a plurality of control signals for controlling the imaging unit; generating an extraction timing of extracting measurement signals from the imaging unit; transmitting the plural control signals to the imaging unit via a signal input/output unit in synchronization with a reference clock; receiving the measurement signals from the imaging unit via the signal input/output unit in synchronization with the reference clock; counting a reception number of the measurement signals from the start of the measurement; and extracting the measurement signal when the reception number of the measurement signals agrees with the extracting timing.

In the imaging device described above, it is possible that the reference clock includes a first reference clock, and a second reference clock which is different form the first reference clock in the frequency, the plural control signals are transmitted to the imaging unit in synchronization with the first reference clock, and the measurement signals are received in synchronization with the second reference clock.

In the imaging device described above, it is possible that the imaging unit is an MRI unit which produces images by nuclear magnetic resonance imaging, and the frequency of the reference clock is in the range of 0.1-2.0 MHz.

The measuring method according to one aspect of the present invention is the measuring method of measuring by a measuring unit comprising: generating a plurality of control signals for controlling the measuring unit; generating an extraction timing of extracting measurement signals from the measuring unit; transmitting the plural control signals to the measuring unit via a signal input/output unit in synchronization with a reference clock; receiving the measurement signals form the measuring unit via the signal input/output unit in synchronization with the reference clock; counting a reception number of the measurement signals from the start of the measurement; and extracting the measurement signal when the reception number of the measurement signals agrees with the extracting timing.

Effects of the Invention

As described above, according to the present invention, the imaging device includes an imaging unit producing images, and a control unit controlling the imaging unit, further comprises: a reference clock unit generating a reference clock; and a signal input/output unit provided between the imaging unit and the control unit and inputting and outputting signals in synchronization with the reference clock generated by the reference clock unit, the control unit comprising: generating means generating a plurality of control signals for controlling the imaging unit and generating an extraction timing of extracting measurement signals from the imaging unit; transmitting means transmitting the plural control signals generated by the generating means to the imaging unit via the signal input/output unit in synchronization with the reference clock; receiving means receiving measurement signals from the imaging unit via the signal input/output unit in synchronization with the reference clock and counting reception times of the measurement signals; and extraction means extracting the measurement signal when the reception times of the measurement signals received by the receiving means agrees with the extraction timing generated by the generating means, whereby images can be produced by generating pulses of stable and accurate time resolution without using special-purpose hardware.

BRIEF DESCRIPTION OF THE DRAWINGS

FIG. 3 is a view of a pulse sequence file (written chart of how a computer will use it) of the imaging system according to the embodiment of the present invention.

FIG. 4 is a first part of control signals of the imaging system according to the embodiment of the present invention.

FIG. 5 is a second part of control signals of the imaging system according to the embodiment of the present invention.

FIG. 6 is a view of an extraction start timetable of the imaging system according to the embodiment of the present invention.

FIG. 7 is a first part of measurement signals of the imaging system according to the embodiment of the present invention.

FIG. 8 is a second part of measurement signals of the imaging system according to the embodiment of the present invention.

FIG. 9 is a view of measurement data of the imaging system according to the embodiment of the present invention.

DETAILED DESCRIPTION OF THE INVENTION

Mode for Carrying Out the Invention

One Embodiment

Figure 1:
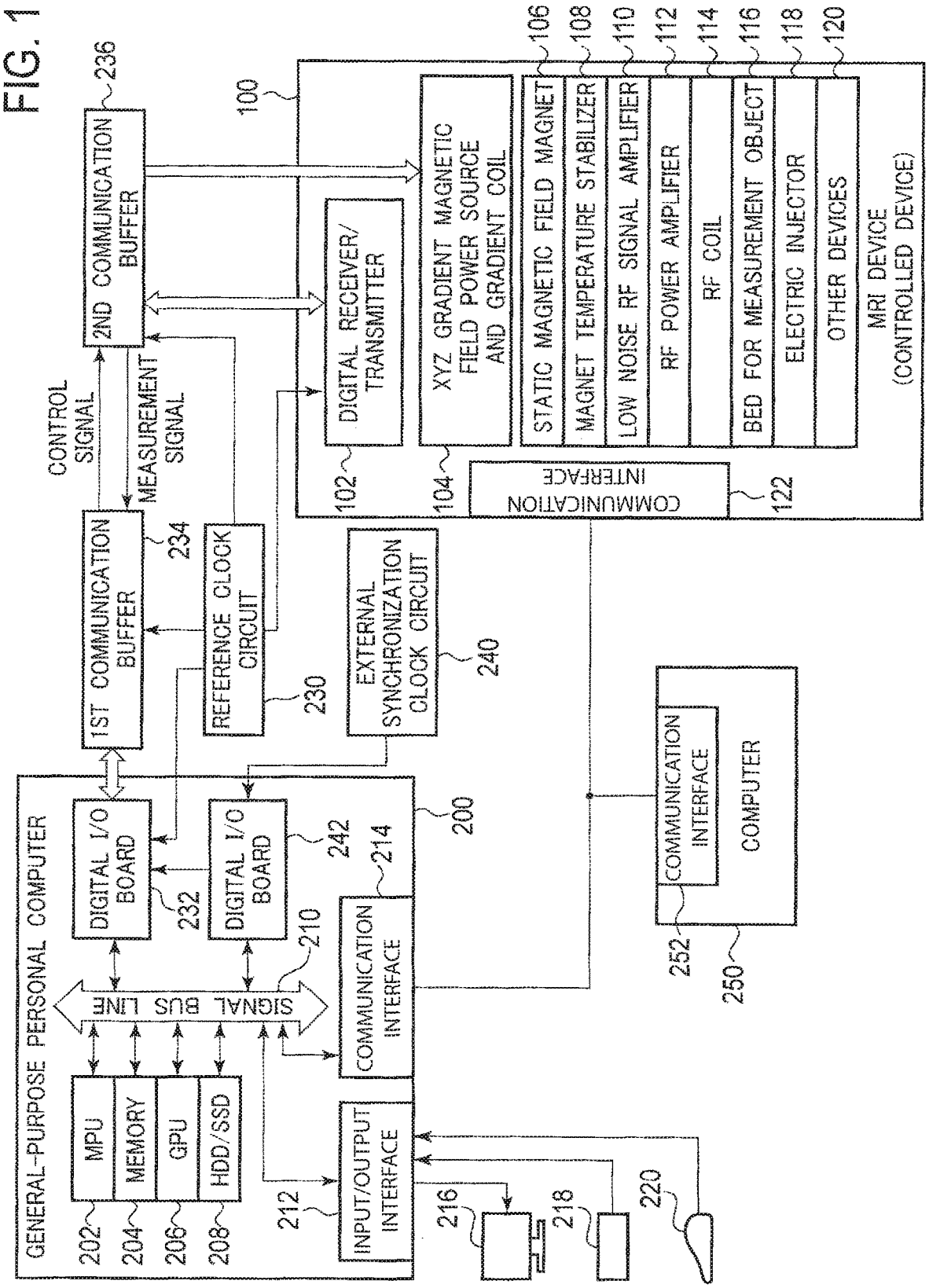
FIG. 1 is a block diagram of the imaging system according to one embodiment of the present invention, which shows the constitution of the imaging system.
Figure 2:
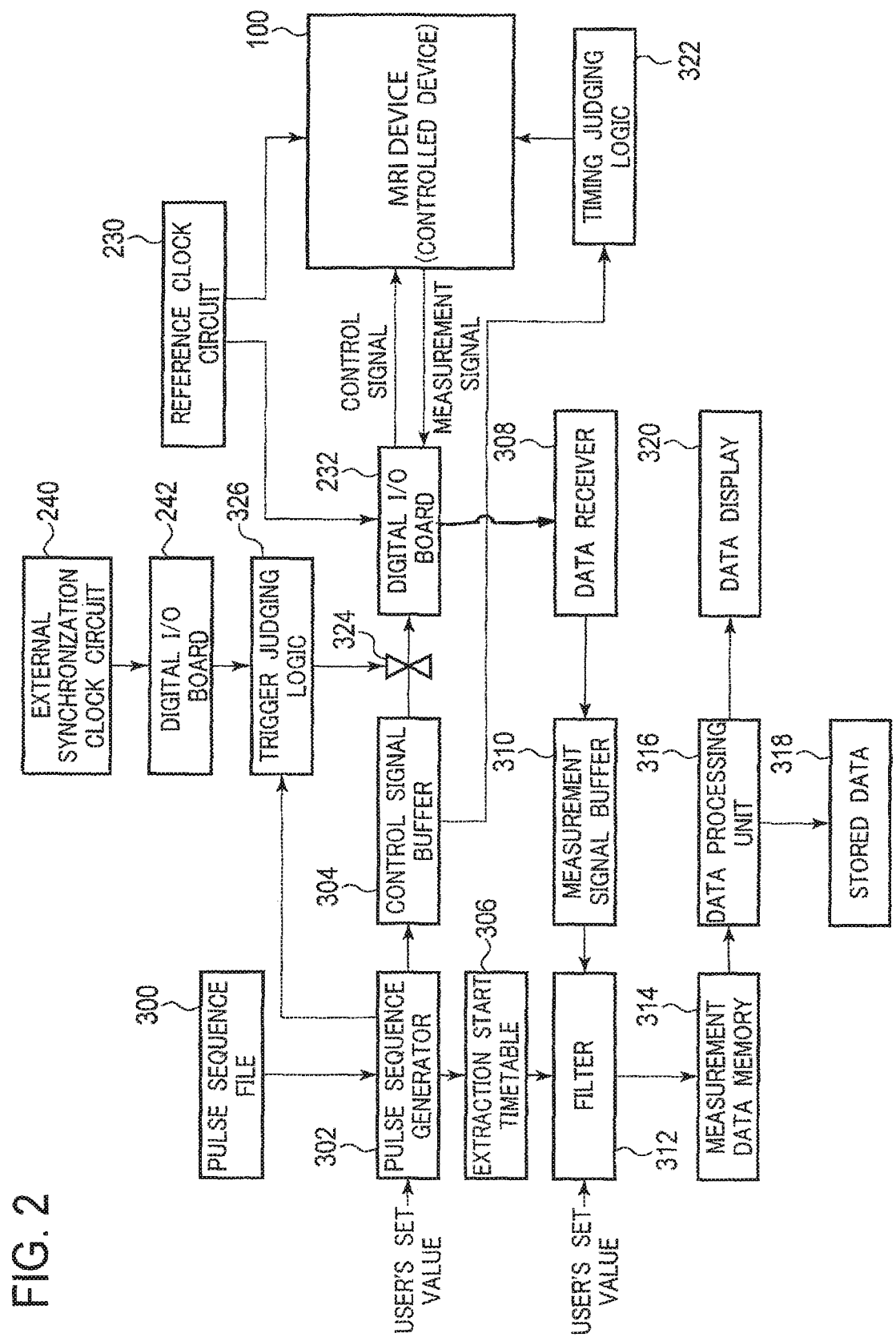
FIG. 2 is a functional block diagram of the imaging system according to the embodiment of the present invention, which shows the operation of the imaging system.

The imaging system according to one embodiment of the present invention will be described with reference to the drawings. FIG. 1 is a block diagram of the physical connections of the imaging system according to the present embodiment, which shows the constitution of the imaging system. FIG. 2 is a functional block diagram of the functional operation of the imaging system according to the present embodiment, which shows the operation of the imaging system. According to the principles of the imaging system according to one embodiment of the present invention, FIG. 1 shows the physical connections and FIG. 2 shows functional connections.

(MRI Imaging System)

As shown in FIG. 1, the imaging system according to the present embodiment comprises an MRI (Magnetic Resonance Imaging) device 100 using the nuclear magnetic resonance (NMR) imaging (MRI) as a device to be controlled, and a general-purpose personal computer 200 as a control device for controlling the device to be controlled.

The MRI device 100 comprises: a digital receiver/transmitter 102 which transmits and receives digital signals, analog transmitted RF pulses and analog received signals; an XYZ gradient magnetic field power source and a gradient coil 104 which includes a power source and a coil for applying XYZ gradient magnetic field; a static magnetic field magnet 106 which applies a static magnetic field; a magnet temperature stabilizer 108 which stabilizes the magnet temperature; an Low noise RF signal amplifier 110 which amplifies RF micro signals; an RF power amplifier 112 which amplifies RF power; an RF coil 114 which receives and transmits RF signals; a bed for measurement object 116 which carries an object-to-be-imaged to a prescribed position; an electric injector 118 which injects a contrast medium in synchronization with pulse sequences; and other devices 120 such as other imaging modalities, devices which operate in the magnetic resonance imaging, etc.

The digital receiver/transmitter 102 has the function of A/D converting MRI signals inputted via the Low noise RF signal amplifier 110, and the A/D converted signals are sequentially transmitted to a second communication buffer 236 in synchronization with a reference clock of 0.1-2.0 MHz from a reference clock circuit 230.

The MRI device 100 further comprises a communication interface 122 for the connection to other devices via USE, LAN, etc.

The general-purpose personal computer 200 comprises an MPU (Micro Processing Unit) 202 which is the main CPU; a memory 204 which is a buffer memory for temporarily storing programs and data necessary for the MPU 202 to make processing; a GPU (Graphic Processing Unit) 206 which makes graphic processing and an HDD (Hard Disk Drive)/SSD (Solid State Drive) memory 208 which stores programs and data. The MPU 202, the memory 204, the GPU 206 and the HDD/SSD memory 208 are mutually connected by a signal bus line 210.

The CPU 206 comprises a computation core specialized for scientific computation to assist the computation processing of the MPU 202 and make computation processing of a measurement soft module having the priority of using the GPU 206 to thereby improve the operational stability of the general-purpose personal computer 200 as a whole.

In the general-purpose personal computer 200, Windows (registered trademark) by Microsoft Corporation, for example, is mounted. The multi-task OS, such as Windows (registered trademark), irregularly executes interruption processing.

In the general-purpose personal computer 200, an input/output interface 212 for connecting input and output devices, and a communication interface 214 for the connection with other devices by USB, LAN, etc. are further mounted. The input/output interface 212 and the communication interface 214 are connected to the signal bus line 210.

To the input/output interface 210, a monitor 216, a key board 218 and a mouse 220 are connected. An operator operates the general-purpose personal computer 200 with the monitor 216, the key board 218 and the mouse 220.

The reference clock circuit 230 generates four (see FIG. 1) reference clocks, at least one of which contains a reference for the synchronous control of the MRI device 100. The reference clock circuit 230 generates a reference clock of a constant period with TCXO (Temperature Compensated Crystal Oscillator) or others. A reference clock of 0.01-100 MHz is generated.

The reference clock may not take the NMR (Nuclear Magnetic Resonance) frequency into consideration. The NMR center frequency is generated and oscillated with the same TCXO that generates the reference clock. The NMR center frequency is used in the digital receiver/transmitter 102. In a case, however, that NMR center frequency is lower than 2 MHz, the reference clock and the NMR frequency are sometimes the same.

A first reference clock signal is preferably 1-100 MHz for the excitation RF pulse and 0.01-1 MHz for the gradient magnetic field pulse, and differs for the respective purposes.

The frequency of a second reference clock signal of the present embodiment is preferably above 0.01 MHz including 0.01 MHz, more preferably, in the range of 0.1-2.0 MHz, and further more preferably, 1.0 MHz.

From the view point of generating an idealistic pulse, it is preferable to increase the time-resolution ability, i.e., to realize 100 MHz which is the maximum frequency. However, when the frequency of the reference clock is higher, the processing quantity of the received/transmitted data is enormous. In a case that the pulse generation is simplified to the max, the MRI will be possible even with the reference clock of 0.01 MHz, but the pulse resolution ability becomes too low.

Then, the reference clock of 1 MHz which satisfies the requirement as the excitation RF pulse and the requirement as the gradient magnetic field pulse is preferable.

From the view point of the data processing quantity and the processing quality of the measurement signals, the reference clock is preferable in the range from 0.1 to 2.0 MHz. In this viewpoint as well, the reference clock of 1 MHz described above is in this range and preferable.

There is a possibility that owing to the development of the computer technology, the desirable reference clock will be raised to about 10 MHz in the near future.

In the general-purpose personal computer 200, separate from the usual input/output interface 212, a general-purpose digital I/O board 232 is provided. The general-purpose digital I/O board 232 is connected to the signal bus line 210.

Into and from the general-purpose digital I/O board 232, control signals for controlling the MRI device 100 are inputted and outputted in synchronization with the first reference clock signal. Into and from the general-purpose digital i/O board 232, measurement signals from the MRI device 100, etc. are inputted and outputted in synchronization with the second reference clock signal.

The digital I/O board 232 operates in synchronization with the reference clock signals as described herein and, when interruption processing takes place in Windows (registered trademark) mounted in the general-purpose personal computer 200, is always stably operative without generating time delays and jitters in the inputted/outputted signals.

A first communication buffer 234 temporarily stores the transmitted data of the control signals transmitted from the digital I/O board 232 and received data of the measurement signals received by the digital I/O board 232.

A second communication buffer 236 temporarily stores the transmitted data of the control signals transmitted from the first communication buffer 234 and the received data of the measurement signals received by the first communication buffer 234.

The second communication buffer 236 is connected to the digital receiver/transmitter 102, the XYZ gradient magnetic field power source and the gradient coil 104, and receives and transmits signals from and to the digital receiver/transmitter 102, and transmits control signals to the XYZ gradient magnetic power source and the gradient coil 104.

The reference clock from the reference clock circuit 230 is supplied to the digital I/O board 232, the first communication buffer 234, the second communication buffer 236 and the digital receiver/transmitter 102 to operate them in synchronization with the reference clock.

An external synchronization clock circuit 240 receives analog inputs, as of heart rates, respirations, the power source clock, etc., and digitally generates a relatively low external synchronization clock, for example, the external synchronization clock of 0.1-60 Hz.

For the heart rates of often a mouse or a man, an external synchronization clock of 0.5-10 Hz is generated, based on inputs from an electrocardiographic monitor, a heart rate meter using infrared radiation.

For the respiration of often a mouse or a man, an external synchronization clock of 0.1-5 Hz is generated, based on the inputs from a pressure sensor using a balloon or others.

For the power source clock, an external synchronization clock of 50 Hz or 60 Hz is generated, based on the inputs from a circuit which digitizes a source AC frequency.

Such interruption processing has the priority over the repetition time TR of the pulse sequence shown in the 11-th row in FIG. 3. By using this function, the repetition time TR can be renewed without changing the pulse sequence file 300. Simply, the same clock as the repetition time TR designated by the pulse sequence in the 11-th row in FIG. 3 may be inputted.

However, it is also possible that said external synchronization clock 240 is judged in real time, and an irregular external synchronization may be generated as when the external synchronization clock 240 is generated for 8 heart rate signals inputted after a one-second blank from the start of a subject patient's respiration.

In the general-purpose personal computer 200, separate from the usual input/output interface 212, a general-purpose digital I/O board 242 is further provided. The general-purpose digital i/O board 242 is connected to the signal bus line 210.

The general-purpose digital I/O board 242 controls the input/output of the signals by the digital I/O board 232 in synchronization with the external synchronization clock 240. This synchronization with the external synchronization clock corresponding to heart rate signal of a man-to-be-detected, measurement signals from the MRI device 100 are inputted and outputted into and from the general-purpose digital I/O board 242.

In the imaging system according to the present embodiment, another general-purpose personal computer 250 is further provided. The general-purpose personal computer 250 is connected to the MRI device 100 and the general-purpose personal computer 200 via a communication interface 252 by USB, LAN, etc.

The general-purpose personal computer 250 reconstructs an image, based on measurement data.

In the present embodiment described above, the reference clock circuit 230 generates one reference clock, and, in synchronization with the reference clock, signals are inputted and outputted into and from the digital I/O board 232, but this is not essential.

The reference clock circuit 230 generates the first reference clock signal and the second reference clock signal which are different from each other in the frequency, whereby the first reference clock signal of 1-10 MHz excitation and the second reference clock signal of 0.1-2.0 MHz gradient are generated.

When control signals for controlling the MRI device 100 are transmitted, the control signals are transmitted in synchronization with the first reference clock, and when measurement signals are received from the MRI device 100, the measurement signals are received in synchronization with the second reference clock.

(Operation of the Imaging System)

Next, the operation of the imaging system according to the present embodiment will be described with reference to the functional diagram of FIG. 2.

In the imaging system according to the present embodiment, images are produced by the MRI device 100, based on a measurement program. To execute the measurement program, a pulse sequence file 300 of pulse sequences described in the text format is prepared.

As shown in FIG. 3, the pulse sequence file 300 is formed of a plurality of pulse sequences described in the text format.

At the top of the pulse sequence file 300, pulse sequences for the initial setting for imaging by the MRI device 100 are arranged.

For example, they are the pulse sequences in the 1st row to the 11th rows of FIG. 3.

The 1st row pulse sequence (:NX 1) stipulates a number of accumulations.

The 2nd row pulse sequence (:DW 5) stipulates a receiver sampling rate (microsecond).

The 3rd row pulse sequence (:NR 2048) stipulates a number of receiver sampling points.

The 4th row pulse sequence (:N0 1) stipulates a number of a phase encode 0.

The 5th row pulse sequence (:N1 128) stipulates a number of a phase encode 1.

The 6th row pulse sequence (:N2 16) stipulates a number of a phase encode 2.

The 7th row pulse sequence (:S0 0) stipulates a step size of the phase encode 0.

The 8th row pulse sequence (:S1 64) stipulates a step size of the phase encode 1.

The 9th row pulse sequence (:S2 64) stipulates a step size of the phase encode 2.

The 10th row pulse sequence (:DU 10) stipulates a number of dummy pulses.

The 11th row pulse sequence (:TR 100) stipulates a repetition time TR [mille second].

Pulse sequences of the imaging are arranged, following the pulse sequences of the initial setting. For example, they are the pulse sequences in the 12th row and the row following the 12th row, of FIG. 3.

The 12th row pulse sequence (00009400 RF 0002) stipulates the transmission of the second RF pulse 9,940 microseconds later from the measurement start.

The 13th row pulse sequence (00010600 GY 8000<-e5) stipulates the renewal and output of a gradient magnetic field GY axis control signal 10,160 microseconds later from the measurement start.

The 14th row pulse sequence (000102200 GX 6E40) stipulates the output of 6E40 to the gradient magnetic field GX axis control signal 10,220 microseconds later from the measurement start.

The 15th row pulse sequence (000102600 GZ 8000<-e6) stipulates the renewal and output of the gradient magnetic field GZ axis control signal 10,260 microseconds later from the measurement start.

The 16th row pulse sequence (000120320 GZ 8000) stipulates the output of 8000 to the gradient magnetic field GZ axis control signal 12,032 microseconds later from the measurement start.

The 17th row pulse sequence (000128260 GY 8000) stipulates the output of 8000 to the gradient magnetic field GY axis control signal 12,826 microseconds later from the measurement start.

The 18th row pulse sequence (000133800 GX 88D4) stipulates the output of 88D4 to the gradient magnetic field GX axis control signal 13,380 microseconds later from the measurement start.

The 19th row pulse sequence (000148800 AD 0000) stipulates the start of receipt by A/D conversion of received signals 14,880 microseconds later from the measurement start.

The 20th row pulse sequence (000302400 GX 8000) stipulates the output of 8000 to the gradient magnetic field GX axis control signal 30,240 microseconds later from the measurement start.

The pulse sequences in from the 12th row to the 18th row, and the 20th row are for operating the MRI device 100 which is to be controlled.

The pulse sequence in the 19th row stipulates the extraction timing of extracting measurement signals from the MRI device 100 which is to be controlled.

In the conventional imaging system, as the extraction timing of extracting measurement signals from the MRI device 100, an actuation signal is transmitted to an A/D converter (not shown) provided in the MRI device 100 via a control line separately provided. The pulse sequence in the 19th row indicates the transmission timing of the actuation signal to such A/D converter (not shown).

In the imaging system according to the present embodiment, the A/D converter (not shown) of the MRI device 100 is kept on, and no control line for the actuation is separately provided. The pulse sequence film of FIG. 3 is for the conventional imaging system. To the contrary, in the present embodiment, the pulse sequence in the 19th row stipulates the extraction timing of extracting a measurement signal form the MRI device 100, which is a control device to be controlled.

A pulse sequence generator 302 which is also referred to herein as pulse signal generator 302 develops control signals from the pulse sequence file 300, and generates a time of starting the extraction of a measurement signal. The pulse signal generator 302 generates an extraction start time timetable that provides times when measurement signals from the imaging unit of the MRI device are extracted, each of the extraction start, times in the extraction start time timetable being an amount of time that has elapsed from a start of a transmission of the control signals.

(Transmission of Control Signal)

First, the transmission of the control signals will be described.

The pulse sequence generator 302 develops pulse sequences of the pulse sequence file 300 stipulating the control of the MRI device 100. Control signals are applied for a fixed time interval based on the reference clock and are stored in the control signal buffer 304 which is the buffer of the timetable of the transmission events.

For example, when the reference clock is 1.0 MHz, as shown in FIGS. 4 and 5, the pulse sequences are developed into control signals of every 1 (one) microsecond (.mu.sec).

To the developed control signals, data number "0" is applied at the start of a measurement operation, i.e., at the start of the transmission of the control signals, and thereafter sequential data numbers "1", "2", "3", . . . are applied. The data numbers of the control signals correspond to a counter N which will be described later.

For example, as shown in FIG. 4, the control signal of data number "0" is "4E18,0000,0000,0000,0000,0000,0000, 0000", the control signal of data number "1" is "4E18,0000, 0000,0000,0000,0000,0000,0000", and the control signal of data number "2" is "4E18,0000,0000,0000,0000,0000,0000, 0000", . . . and the sequentially following control signals are generated.

The respective control signals are segmented, and in the examples of FIGS. 4 and 5, "4E18" indicates the start of the respective segmented control signals.

The developed control signals are stored in the control signal buffer 304. The control signal buffer 304 is, e.g., the first communication buffer 234 in FIG. 1.

Based on the data number of each control signal, the time from the start of the transmission of the control signal when the control signal is to be transmitted can be known. For example, as shown in FIG. 4, the control signal having data number "43" is to be transmitted 43 microseconds later after the start of the transmission of the control signal. For example, as shown in FIG. 5, the control signal of data number "14860" is to be transmitted 14860 microseconds later, i.e., 14.86 milliseconds later from the start of the transmission of the control signal.

The control signals stored in the control signal buffer 304 are sequentially transmitted to the MRI device 100, which is the device to be controlled, in synchronization with the reference clock.

Thus, the MRI device 100, which is the device to be controlled, is controlled, based on the respective pulse sequence activation of control signal timing of the pulse sequence file 300.

Low speed control signals which need not be transmitted via the digital I/O board 232 are generated by the pulse sequence generator 302, stored in the control signal buffer 304, decided by a timing judging logic 322 and transmitted to the MRI device 100, which is the device to be controlled.

The general-purpose personal computer 200 and the computer 250 can know via the communication interfaces the control signals and also status of all the components of the MRI device 100.

The low speed control signals which need not be transmitted via the digital I/O board 232 are, e.g., a signal that turns on lamps, a signal that changes the transmission/reception gains of the digital transmitter/receiver 102, a signal that changes one of filter commands to a lower speed one thereof, and a signal for the control value command of a temperature stabilizer of the magnet, etc.

Between the control signal buffer 304 and the digital I/O board 232, there is a valve 324 configured for opening and closing with respect to the transmission/reception of the signals.

The valve 324 is opened and closed by a trigger judging logic 326. The trigger judging logic 326 opens and closes the valve 324, taking into account the external synchronization clock circuit 240 such as heart rate signals, respirations, the power source lock, etc. received via the digital I/O board 242, and an external synchronization clock circuit reception timing received from the pulse sequence generator 302.

The operation of the valve 324 is commanded by trigger judging logic 326. For example, the command signal data point (000312400 EX 0000) for commanding the operation of the valve 324 stipulates the closure of the valve 324 31,240 microseconds later from the start of a measurement and the operation of opening the valve 324 in accordance with the command of the trigger judging logic 326 100,000 microseconds later. In this case, the valve 324 is closed 131,240 microseconds later from the start of the measurement.

A transmitter is configured to transmit the plurality of control signals generated by the pulse signal generator 302 to the imaging unit of the MRI device via the digital signal input/output in synchronization with the first reference clock signal.

A first storage unit is configured to store the time elapsed from the start of the transmission of the control signals.

(Extraction of Measurement Signals)

Then, the extraction of the measurement signals will be described.

The pulse sequence generator 302 generates a time of starting the extraction of measurement signals, based on the pulse sequences stipulating the times of extracting measurement signals from the MRI device 100 of the pulse sequence file 300, and stores the times in an extraction start timetable 306. The extraction start timetable 306 is formed by, e.g., the first communication buffer 234 in FIG. 1.

For example, based on the pulse sequence (000148800 AD 0000) in the 18th row, "14,880 microseconds" is generated as the extraction start time of the measurement signals and, as shown in FIG. 6, is stored in the 1st row of the extraction start timetable 306.

In the same way, based on the pulse sequences stipulating the extraction times of extracting measurement signals, times of starting the extraction of the measurement signals are generated and sequentially stored in the extracted start timetable 306. Resultantly, the extraction start timetable as exemplified in FIG. 6 is generated.

As shown in FIG. 2, the measurement signals from the MRI device 100 are received by the digital receiver 308 via the digital I/O board 232 in synchronization with the reference clock and stored in the measurement signal buffer 310.

For example, when the reference clock is 1.0 MHz, as shown in FIGS. 7 and 8, the measurement signals are received every 1 (one) microsecond.

The data number "0" is applied to the measurement signal at the start of the measurement operation, i.e., at the start of the reception of the measurement signals, and thereafter data numbers "1", "2" and "3", ... are sequentially applied to the measurement signals. The data numbers of the measurement signals correspond to a counter "M" is which will be described later.

As exemplified in FIG. 7, the measurement signal of data number "0" is "B1E7,0000,−54,−26,0,1,0000,0000", and the measurement signal of data number "1" is "B1E7,0000,−54,−21,0,2,0000,0000", the measurement signal of data number "2" is "B1E7,0000,−54,−16,0,3,0000,0000". Such sequentially following measurement signals are stored in the measurement signal buffer 310.

The respective measurement signals are segmented, and in the examples of FIGS. 7 and 8, "B1E7" indicates the start of the segmented measurement signals.

Based on the data numbers of the measurement signals, the times of the reception of the measurement signals from the start of the reception of the measurement signals can be known. For example, as shown in FIG. 7, the measurement number (B1E7,0000,−11,−40,0,44,0000,0000" of data number "43" is the measurement signal received after 43 microseconds from the start of the measurement signal reception. For example, as shown in FIG. 8, the measurement signal "B1E7,0000,−6,−30,0,14861,00000000" of data number "14860", i.e., 14.86 milliseconds is the measurement signal received after 14860 microseconds from the measurement signal reception start.

The filter 312 shown in FIG. 2 extracts measurement signals necessary for the MRI from the measurement signals stored in the measurement signal buffer 310, based on the extraction start time stored in the extraction start timetable 306, and stores the measurement signal in a measurement data memory 314.

For example, in the case of the extraction start timetable 306 of FIG. 6, "14,880 microseconds" is stored in the 1st row, the data numbers of the measurement signals stored in the measurement signal buffer 310 are scanned, and when the data number becomes "14880", the extraction of the measurement signal starts. Measurement signals are extracted for a certain period of time from the extraction start time "14,880 microseconds", i.e., up to data number "25115" which is after 5 microseconds.times.2048 points-5 microseconds=10,235 microseconds. That is, when measurement signals have the data numbers from "14880" to "25115", the measurement signals are extracted.

Subsequently, for "114,880 microseconds" stored in the second row of the extraction start timetable 306, the data numbers of the measurement signals stored in the measurement signal buffer 310 are scanned, and when the data number becomes "114880", the extraction of the measurement signal is started. And, the measurement signals for a certain period of time from the extraction start time, i.e., after "114,880 microseconds", i.e., up to data number "125115". That is, when measurement signals have data numbers "114880"-"125115", the measurement signal are extracted.

In the same way, based on the extraction start times indicated in the extraction start timetable 306, measurement signals are sequentially extracted.

Resultantly, as exemplified in FIG. 9, the measurement data of a certain period of time, e.g., 10,235 microseconds, from the extraction start time "14,880 microseconds", corresponding to the extraction start times of the extraction start timetable 306 of FIG. 6, are extracted. The measurement data of a certain period of time, e.g., 10,235 microseconds, from the extraction start time "114,880 microseconds", corresponding to the extraction start times of the extraction start timetable 306 of FIG. 6, are extracted.

The measurement data stored in the measurement data memory 314 are subjected to processing of noise removal, image reconstruction, etc. are stored as stored data 318 in the HDD/SSD memory 208 or are displayed as an data display 320 on the personal computer 250.

As shown in FIG. 2, into the pulse sequence generator 302 and the filter 312, user's command values can be suitably inputted from the outside.

For example, user's command values are inputted into the pulse sequence generator 302 from the outside thereby to give information prior to the pulse sequence file 300, to command whether or not the external synchronization clock circuit is used, or to command 3-axes rotation angles of the XYZ axes outputs of the gradient magnetic field pulses.

User's command values are inputted from outside into the filter 312 thereby to command a tap number of the FIR filter, or to command a cut-off frequency, and command other signal processing.
A filter is configured to extract measurement signals with times within a predetermined period of time from when the time of the measurement signal agrees with the time of the extraction start time stored in the extraction start time timetable.

(Measurement Operation Flow of the Imaging System)

Figure 10:
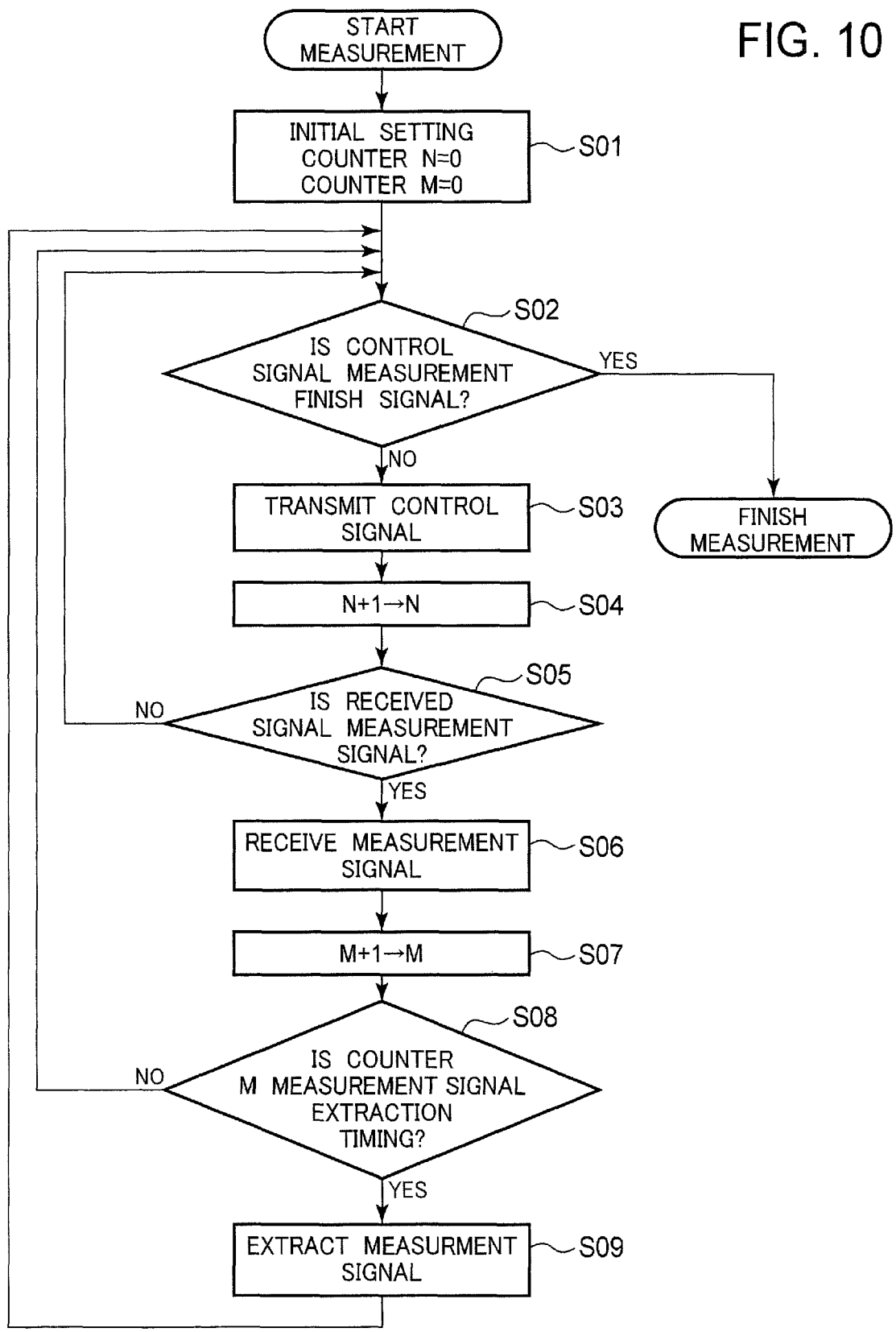
FIG. 10 is a flow chart of the measurement operation of the imaging system according to the embodiment of the present invention.

Next, the measurement operation flow of the imaging system according to the present embodiment will be described with reference to the flow chart of FIG. 10.

When a measurement of the imaging system is started, as the initial setting, the counter N and the counter M are reset at 0 (Step S01). The counter N corresponds to the data number of a control signal, and the counter M corresponds to the data number of a measurement signal.

First, it is judged whether or not a control signal transmitted from the control signal buffer 304 to the digital I/O board 232 is a measurement finishing signal (Step S02). In the present embodiment, the measurement finishing signal for finishing a measurement is prepared as one control signal.

In Step S02, when the control signal is judged to be the measurement finishing signal, the measurement is immediately finished.

In Step S02, when the control signal is judged not to be the measurement finishing signal, said control signal is transmitted to the MRI device 100, which is a device to be controlled (Step S03), and 1 is added to the counter N.

Then, it is judged whether the received signal the digital I/O port 232 from the MRI device 100 is a measurement signal (Step S06). The measurement signals are segmented, and "B1E7" indicates the start of the respective segmented measurement signals, and when "B1E7" is detected, said received signal is judged to be a measurement signal.

When the received signal is judged not to be a measurement signal in Step S05, the step is returned to Step S02.

When the received signal is judged to be a measurement signal in Step S05, said received signal is received as a measurement signal (Step S06), and 1 is added to the counter M.

Next, it is judged whether or not the counter M is a measurement signal extraction timing (Step S08).

When the counter M is judged not to be a measurement signal extraction timing in Step S08, the step is returned to Step S02.

When the counter M is judged to a measurement signal extraction timing in Step S08, said measurement signal is extracted (Step S09), and the step is returned to Step S02.

In Step S08, a timing of extracting data from the extraction start timetable 306, i.e., a period of time from the measurement start time, and the counter M judges whether or not it is a measurement signal extraction timing.

For example, in the extraction start timetable 306 of FIG. 6, as described above, the counter M is from "14880" to "25115", based on "14,880 microseconds" in the 1st row, the measurement signals are extracted. Based on "14,880 microseconds" in the 2nd row, the counter M is from "114880" to "125115", the measurement signals are extracted. In the same way, measurement signals are sequentially extracted based on the extraction start times in the extraction start timetable 306.

The above-described processing is repeated, and the counter N counts a number of controls signals transmitted to the MRI device 100, the counter M counts a number of measurement signals received from the MRI device 100, and based on the counter M, the measurement signals are extracted.

As described above, a number of measurement signals from the measurement start time is counted, whereby measurement data can be extracted from measurement signals without separately providing a control line for actuating the A/D converter (not shown) in the MRI device 100.

In the present embodiment, the counter N, which counts a number of control signals, and the counter M, which counts a number of measurement signals are separately provided, whereby the count of the control signals and the count of the measurement signals are independently made. This produces the following advantage.

For example, when no measurement signal is detected in Step S05, the counter M is counted up. In this case, a count value of the counter M is smaller than a count value of the counter N, but the processing is correctly carried on.

The reference clock circuit 230 generates a first reference clock and a second reference clock which are different from each other in the frequency. In synchronization with the first reference clock, control signals are transmitted to the MRI device 100. In synchronization with the second reference clock, measurement signals from the MRI device 100 are received. The counter N counts a number of control signals transmitted in synchronization with the first reference clock. The counter M counts a number of measurement signals received in synchronization with the second reference clock.

The measurement processing of the imaging system of the flow chart described above is one example and is not essential. For example, it is possible that Step S03, Step S06 and Step S09 are multitasked or multithreaded without obstructing the operation of the measurement to independently operate. Especially, in Step S06, by using vast data stored in Step S06, even after an experiment, data may be collected retrospectively from a time when the experiment finishes to be analyzed. It is possible that a timing of the counter M is changed after an experiment has finished, and measurement signals are extracted. In Step S06, live data of measurement signals may be discarded or preserved.

A receiver is configured to receive measurement signals from the imaging unit of the MRI device via the digital signal input/output unit in synchronization with the second reference clock signal.

A second storage unit is configured to store the measurement signals received in synchronization with the second reference clock signal by the receiver, with a time elapsed from a start of a reception of the measurement signals.

A third storage unit is configured to store the measurement signals within the predetermined period of time extracted by the filter.

EXAMPLE

Figure 11:
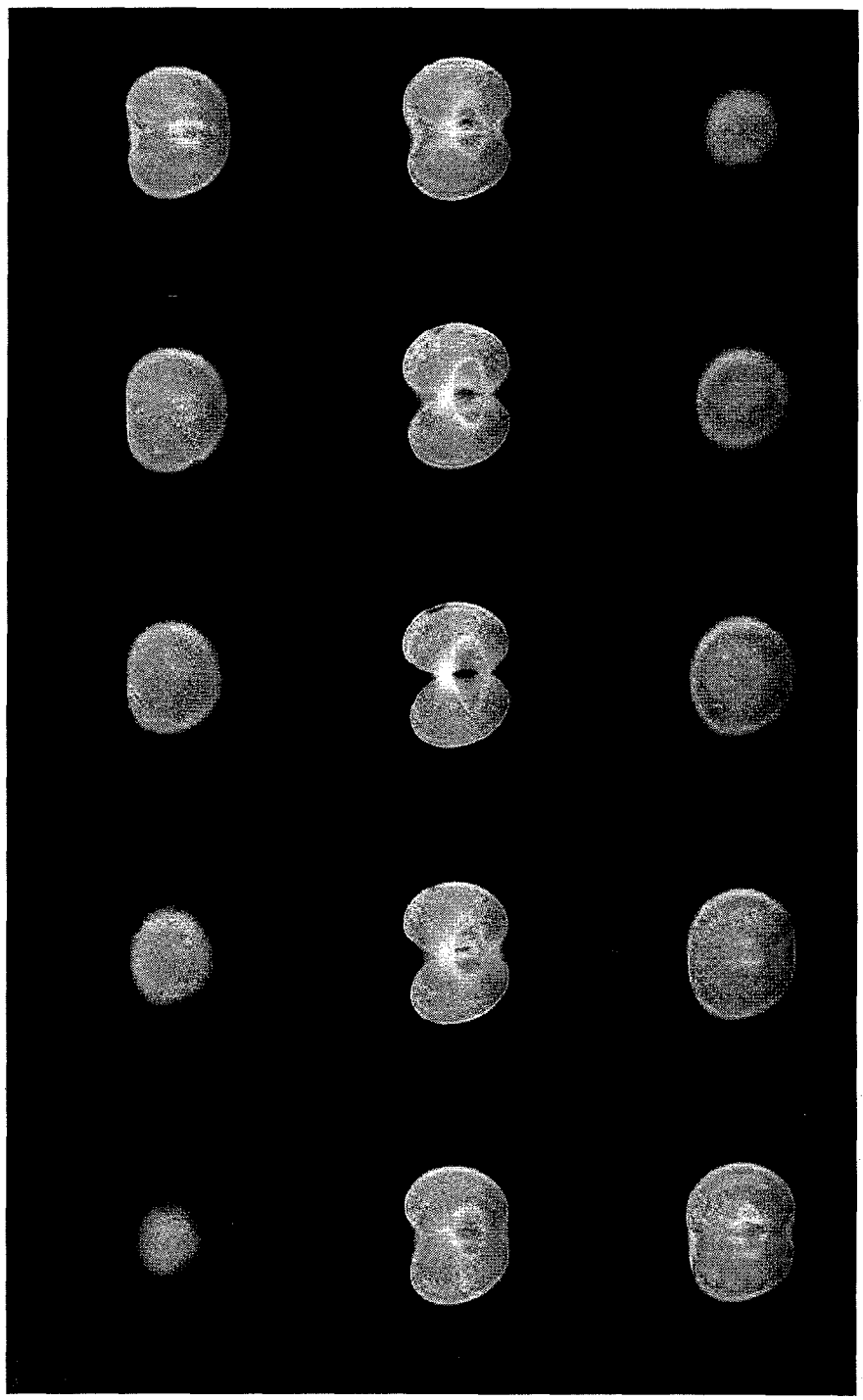
FIG. 11 is a view of the measurement result of the imaging system according to the embodiment of the present invention.

Sections of an apple were imaged by the imaging system according to the present embodiment. The result of imaging the apple is shown in FIG. 11. As shown in FIG. 11, the present embodiment could provide good images.

(Modification)

The present invention is not limited to the above-described embodiment and can cover other various modifications.

In the present embodiment, the present invention is applied to the imaging system using the MRI device, but this is not essential. For example, the present invention may be applied to imaging systems using X-ray CT devices, supersonic CT devices, PET-CT devices, etc. The present invention may be applied not only to the imaging systems but also to any measuring system, such as semiconductor device steppers, food manufacturing devices, advanced testing devices, machine tools such as NC lathes, etc., configuration shaping measuring devices, 3-dimensional configuration mapping devices, configuration measuring devices, resonance measuring devices, distribution measuring devices, physical measuring devices, distribution observation devices, etc.

In the above-described embodiment, a user prepares the pulse sequence file in advance, but this is not essential. For example, the data processing unit 316 automatically generates a pulse sequence file to realize an optimum operational state of the device 100 to be controlled. In this case, the application scope of the present invention is not limited to the devices described above. The present invention may be applied to the automatic driving devices of cars, aircraft, etc.

In the specification of the present application, "measurement" includes any measurement, such as imaging objects, measurement of configurations of objects, detection of objects, measurement and detection of characteristics of objects, measurement of physical quantities, detection of physical quantities, etc.

REFERENCE NUMBERS

100 MRI device
200 general-purpose personal computer
102 digital receiver/transmitter
104 XYZ gradient magnetic field power source and gradient coil
106 static magnetic field magnet
108 magnet temperature stabilizer
110 Low noise RF signal amplifier
112 RF power amplifier
114 RF coil
116 bed for measurement object
118 electric injector
120 other devices
122 communication interface
202 MPU
204 memory
206 GPU
208 HDD/SSD memory
210 signal bus line
212 input/output interface
213 communication interface
216 monitor
218 key board
220 mouse
230 reference clock circuit
232 digital I/O board
234 first communication buffer
236 second communication buffer
240 external synchronization clock circuit
242 digital/O board
300 personal sequence file
302 personal sequence generator
304 control signal buffer
306 extraction start timetable
308 digital receiver
310 measurement signal buffer
312 filter
314 measurement data memory
316 data processing unit
318 stored data
320 data display
322 timing judging logic
324 valve
326 trigger judging logic

What is claimed is:

1. An MRI device including an imaging unit producing MRI images, and a control unit controlling the imaging unit of the MRI device, further comprising:
a reference clock unit configured to generate a first reference clock signal as well as a second reference clock signal, wherein the first reference clock signal is in the range of 1-100 MHz and is utilized with excitation RF pulses, and wherein the second reference clock signal is in the range of 0.01-1 MHz and is utilized with gradient magnetic field pulses; and
a digital signal input/output unit provided between the imaging unit of the MRI device and a signal bus line of the control unit and inputting and outputting signals in synchronization with the second reference clock signal generated by the reference clock unit,
the control unit comprising:
a pulse signal generator that is configured to generate a plurality of control signals for controlling the imaging unit of the MRI device while also being configured to generate an extraction start time timetable that provides times when measurement signals from the imaging unit of the MRI device are extracted, each of the extraction start times in the extraction start time timetable being an amount of time that has elapsed from a start of a transmission of the control signals;
a first storage unit that is configured to store the time elapsed from the start of the transmission of the control signals;
a transmitter that is configured to transmit the plurality of control signals generated by the pulse signal generator to the imaging unit of the MRI device via the digital signal input/output unit in synchronization with the first reference clock signal;
a receiver that is configured to receive measurement signals from the imaging unit of the MRI device via the digital signal input/output unit in synchronization with the second reference clock signal;
a second storage unit that is configured to store the measurement signals received in synchronization with the second reference clock signal by the receiver, with a time elapsed from a start of a reception of the measurement signals;
a filter that is configured to extract measurement signals with times within a predetermined period of time from when the time of the measurement signal agrees with the time of the extraction start time stored in the extraction start time timetable; and
a third storage unit that is configured to store the measurement signals within the predetermined period of time extracted by the filter.

2. The MRI device according to claim 1, wherein
the pulse signal generator
generates the plurality of control signals for controlling the imaging unit of the MRI device, based on a 1st pulse sequence for controlling the imaging unit of the MRI device, and
extracts the measurement signals from the imaging unit of the MRI device, based on a 2nd pulse sequence for extracting the measurement signals from the imaging unit of the MRI device.

3. The MRI device according to claim 1, wherein
the transmitter transmits the plurality of control signals to the imaging unit of the MRI device in synchronization with the first reference clock signal, and
the receiver receives the measurement signals in synchronization with the second reference clock signal.

4. The MRI device according to claim 1, wherein the imaging unit of the MRI device produces images by nuclear magnetic resonance imaging.

5. The MRI device according to claim 1, further comprising
an external synchronization clock unit generating an external synchronization clock signal,
the control unit further comprising
an external synchronization means controlling signal input/output by the signal input/output unit in synchronization with the external synchronization clock signal generated by the external synchronization clock unit.

6. An MRI device including a measuring unit for measurement of data and a control unit controlling the measuring unit of the MRI device, further comprising:
a reference clock unit configured to generate a first reference clock signal as well as a second reference clock signal, wherein the first reference clock signal is in the range of 1-100 MHz and is utilized with excitation RF pulses, and wherein the second reference clock signal is in the range of 0.01-1 MHz and is utilized with gradient magnetic field pulses; and
a signal input/output unit provided between the measuring unit of the MRI device and a signal bus line of the control unit and inputting and outputting signals in synchronization with the reference clock signal generated by the second reference clock unit,
the control unit comprising:
a pulse signal generator that is configured to generate a plurality of control signals for controlling the measuring unit of the MRI device while also being configured to generate an extraction start time timetable that provides times when measurement signals from the measuring unit of the MRI device are extracted, each of the extraction start times in the extraction start time timetable being an amount of time that has elapsed from a start of a transmission of the control signals;
a first storage unit that is configured to store the time elapsed from the start of the transmission of the control signals;
a transmitter that is configured to transmit the plurality of control signals generated by the pulse signal generator to the measuring unit of the MRI device via the signal input/output unit in synchronization with the first reference clock signal;
a receiver that is configured to receive measurement signals from the measuring unit of the MRI device via the signal input/output unit in synchronization with the second reference clock signal;
a second storage unit that is configured to store the measurement signals received in synchronization with the second reference clock signal by the receiver, with a time elapsed from a start of a reception of the measurement signals;
a filter that is configured to extract measurement signals with times within a predetermined period of time from when the time of the measurement signal agrees with the time of the extraction start time stored in the extraction start time timetable; and
a third storage unit that is configured to store the measurement signals within the predetermined period of time extracted by the filter.

7. An imaging method of producing images by an MRI device including an imaging unit producing MRI images, and a control unit controlling the imaging unit of the MRI device, the imaging method comprising:
generating a plurality of control signals for controlling the imaging unit of the MRI device;
generating an extraction start time timetable that provides times when measurement signals from the imaging unit of the MRI device are extracted, each of the extraction start times in the extraction start time timetable being an amount of time that has elapsed from a start of a transmission of the control signals;
storing the time elapsed from the start of the transmission of the control signals;
transmitting the plurality of control signals to the imaging unit of the MRI device via a signal input/output unit in synchronization with a first reference clock signal, wherein the signal input/output unit is provided between the imaging unit and a signal bus line of the control unit, wherein the frequency of the first reference clock signal is in the range of 1-100 MHz and a second reference clock signal is in the range of 0.01-1 MHz;
receiving the measurement signals from the imaging unit of the MRI device via the signal input/output unit in synchronization with the second reference clock signal;
storing the measurement signals received in synchronization with the second reference clock signal, with a time elapsed from a start of a reception of the measurement signals;
extracting measurement signals with times within a predetermined period of time from when the time of the measurement signal agrees with the time of the extraction start time stored in the extraction start time timetable; and
storing the extracted measurement signals within the predetermined period of time in a measurement data memory.

8. The imaging method according to claim 7, wherein
the second reference clock signal is different from the first reference clock signal in the frequency,
the plurality of control signals are transmitted to the imaging unit of the MRI device in synchronization with the first reference clock signal, and
the measurement signals are received in synchronization with the second reference clock signal.

9. The imaging method according to claim 7, wherein the imaging unit of the MRI device produces images by nuclear magnetic resonance imaging.

10. A measuring method of measuring by an MRI device including a measuring unit, and a control unit controlling the measuring unit of the MRI device, the control unit performing the measuring method comprising:
generating a plurality of control signals for controlling the measuring unit of the MRI device;

generating an extraction start time timetable that provides times when measurement signals from the measuring unit of the MRI device are extracted, each of the extraction start times in the extraction start time timetable being an amount of time that has elapsed from a start of a transmission of the control signals;

storing the time elapsed from the start of the transmission of the control signals;

transmitting the plurality of control signals to the measuring unit of the MRI device via a signal input/output unit in synchronization with a first reference clock signal, wherein the signal input/output unit is provided between the measuring unit and a signal bus line of the control unit, wherein the frequency of the first reference clock signal is in the range of 1-100 MHz and a second reference clock signal is in the range of 0.01-1 MHz;

receiving the measurement signals from the measuring unit of the MRI device via the signal input/output unit in synchronization with the second reference clock signal;

storing the measurement signals received in synchronization with the second reference clock signal, with a time elapsed from a start of a reception of the measurement signals;

extracting measurement signals with times within a predetermined period of time from when the time of the measurement signal agrees with the time of the extraction start time stored in the extraction start time timetable; and storing the extracted measurement signals within the predetermined period of time in a measurement data memory.

* * * * *